United States Patent

Böhshar et al.

[11] Patent Number: 5,283,350
[45] Date of Patent: Feb. 1, 1994

[54] ARYL ESTERS OF PHOSPHONOUS HALIDES AND A PROCESS FOR THE PREPARATION THEREOF

[75] Inventors: Manfred Böhshar, Kelkheim/Taunus; Hans-Jerg Kleiner, Kronberg/Taunus, both of Fed. Rep. of Germany

[73] Assignee: Hoechst Aktiengesellschaft, Frankfurt am Main, Fed. Rep. of Germany

[21] Appl. No.: 966,041

[22] PCT Filed: Jun. 19, 1991

[86] PCT No.: PCT/EP91/01123
§ 371 Date: Dec. 30, 1992
§ 102(e) Date: Dec. 30, 1992

[87] PCT Pub. No.: WO92/00304
PCT Pub. Date: Jan. 9, 1992

[30] Foreign Application Priority Data

Jul. 2, 1990 [DE] Fed. Rep. of Germany ....... 4021194

[51] Int. Cl.$^5$ .............................................. C07F 9/42
[52] U.S. Cl. .................................. 558/197; 558/202
[58] Field of Search ........................ 558/197, 202, 134

[56] References Cited

U.S. PATENT DOCUMENTS

| | | | |
|---|---|---|---|
| 3,503,923 | 3/1970 | Petrella et al. | 524/407 |
| 4,477,608 | 10/1984 | Bäbler et al. | 523/215 |
| 4,751,321 | 6/1988 | Mann et al. | 558/134 |
| 4,959,406 | 9/1990 | Foltin et al. | 524/413 |

FOREIGN PATENT DOCUMENTS 0004026 9/1979 European Pat. Off. .
0247765 12/1987 European Pat. Off. .
0327384 8/1989 European Pat. Off. .
0456471 11/1991 European Pat. Off. .

*Primary Examiner*—Mary C. Lee
*Assistant Examiner*—Michael G. Ambrose
*Attorney, Agent, or Firm*—Connolly and Hutz

[57] ABSTRACT

Aryl esters of phosphonous halides of the formula I

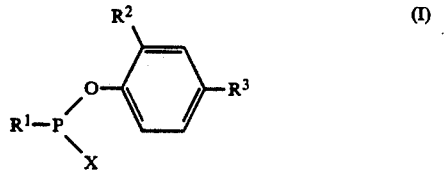

in which
R' is a phenyl or benzyl radical which bears 1 to 3 substituents, α-methylbenzyl, α, α-dimethylbenzyl, naphthyl or a naphthyl radical bearing 1 to 5 substituents, where the substituents are identical or different and are a non-aromatic hydrocarbon radical, an alkoxy radical or alkylthio radical each having 1 to 8 carbon atoms, aryl or aryloxy each having 6 to 10 carbon atoms or halogen having an atomic number from 9 to 35,
$R^2$ is a non-aromatic hydrocarbon radical having 1 to 18 carbon atoms, aryl, arylmethyl, arylethyl or arylisopropyl, where each aryl contains 6 to 10 carbon atoms,
$R^3$ is hydrogen or one of the groups mentioned under $R^2$, and
X is chlorine or bromine.

The invention further relates to a process for the preparation of aryl esters of phosphonous halides of the formula I.

2 Claims, No Drawings

ARYL ESTERS OF PHOSPHONOUS HALIDES AND A PROCESS FOR THE PREPARATION THEREOF

The present invention relates to novel aryl esters of phosphonous halides and to a process for the preparation thereof.

Aryl esters of phosphonous halides are valuable intermediates which, for example, are used as starting materials for the synthesis of industrially interesting phosphonous ester amides, such as are, for example, described in European Laid-Open Application 42, 359, or of phosphonous diesters.

For the preparation of such compounds, phosphonous dihalides have long been used as starting materials, which, for example, are reacted with molar amounts of an alcohol in the presence of a tertiary amine (Houben-Weyl, "Methoden der organischen ChemieII", [Methods in Organic Chemistry], Phosphorus compounds El, p. 285 (1982)).

The serious disadvantage of this process lies in the difficult preparation of the phosphonous dihalides required as precursors, as a result of which this method has not achieved industrial importance. For example, of the aromatic derivatives, only phenyldichlorophosphine is an industrially available product, by means of which alone derivatives of benzenephosphonous acid are accessible.

There was therefore considerable interest in novel aryl esters of phosphonous halides and in industrially more expedient processes for their preparation, which do not have disadvantages of this type.

The present invention relates to aryl esters of phosphonous halides of the formula I (see patent claim 1), in which $R^1$ is a phenyl or benzyl radical which bears 1 to 3 substituents, a-methylbenzyl, $\alpha,\alpha$-dimethylbenzyl, naphthyl or a naphthyl radical bearing 1 to 5 substituents, where the substituents are identical or different and are a non-aromatic hydrocarbon radical, an alkoxy radical or alkylthio radical each having 1 to 8 carbon atoms, aryl or aryloxy each having 6 to 10 carbon atoms or halogen having an atomic number from 9 to 35, $R^2$ a non-aromatic hydrocarbon radical having 1 to 18 carbon atoms, aryl, arylmethyl, arylethyl or arylisopropyl, where each aryl contains 6 to 10 carbon atoms, $R^3$ is hydrogen or one of the groups mentioned under $R^2$, and X is chlorine or bromine.

With regard to industrial production, compounds having X=chlorine are clearly particularly preferred.

Furthermore, those compounds in which $R^1$ is unsubstituted or substituted naphthyl are also particularly preferred.

In the compounds according to the invention of the formula I, $R^1$ is for example a phenyl or benzyl radical, which bears 1 to 3 substituents, such as the $C^1-C_8$-alkyl, $C_1-C_8$-alkoxy, $C_1-C_8$-alkylthio radical such as the alkyl radicals mentioned in detail under R2 having 1 to 8 carbon atoms and the corresponding alkoxy radicals and alkylthio radicals, or $C_5-C_8$-cycloalkyl, phenyl, phenoxy and/or halogen. Radicals which may specifically be mentioned are the tolyl, dimethylphenyl, trimethylphenyl, tertbutylphenyl, anisyl and naphthyl radicals, which can further bear up to 2 alkyl carbon atoms, and the various biphenyl radicals, benzyl, α-methylbenzyl and α, α-dimethylbenzyl. Obviously, the substituents in $R^1$ can only be combined in a manner such that no steric hindrance occurs. If $R^1$ contains 3 substituents, no more than 5 carbon atoms should be contained in the two o-positions together.

Suitable $R^2$ radicals are, for example, non-aromatic hydrocarbon radicals having 1 to 18 carbon atoms, such as alkyl or cycloalkyl, and also aromatic radicals which have 6 to 18 carbon atoms including aliphatic groups, no more than 10 carbon atoms being part of an aromatic ring system. The $R^2$ radicals preferably contain 4 to 12 and in particular 6 to 10 carbon atoms. In detail, suitable nonaromatic hydrocarbon radicals are alkyl such as methyl, ethyl, the various propyl, butyl, pentyl, hexyl, octyl, decyl, dodecyl, hexadecyl and octadecyl radicals, and cycloalkyl having 5 to 10 carbon atoms such as cyclopentyl, cyclohexyl, cycloheptyl and cyclohexylmethyl (ie. both the hydrogenated benzyl radical and also the methyl cyclohexyl radical); $C_8-C_{10}$-aryl and arylmethyl can further be mentioned, the term aryl including in each case alkylaryl, bearing at most three of the substituents mentioned under $R^1$, and, including these, having at most 14 carbon atoms.

When the radical $R^2$ is an alkyl radical, tertiary alkyl radicals having 4–10 carbon atoms, such as tert-butyl, 2-methyl-2-butyl, 2-methyl-2-pentyl and 2-ethyl-2-butyl are particularly preferred. other preferred compounds are those in which $R^2$ is phenyl, benzyl, α-methylbenzyl and α, α-dimethylbenzyl.

The present invention further relates to a process for the preparation of an aryl ester of a phosphonous halide of the formula I which comprises, in a first step, first reacting a hydrocdrbon halide $R^1$—Hal, in which $R^1$ has the abovementioned meaning and its halogen has an atomic weight of at least 35, but is preferably bromine, with at least a stoichiometric amount of magnesium under Grignard conditions, that is expediently with intimate mixing, to give the corresponding Grignard compound $R^1$-Mg-Hal and, in a second step, further reacting this with the aryl ester of the phosphorous dihalide of the formula II (see patent claim 4), in which the radicals $R^2$ and $R^3$ and X have the abovementioned meaning, with the formation of the aryl ester of the phosphonous halide I.

The first step of the process according to the invention which can per se be carried out in any conventional manner, is preferably carried out in an aprotic, organic solvent such as an ether, for example diethyl, dipropyl or diisopropyl ether, ethylene glycol dimethyl or ethylene glycol diethyl ether, diethylene glycol dimethyl or diethylene glycol diethyl ether, methyl tert-butyl ether, dioxan or tetrahydrofuran.

Since the Grignard compounds and the starting materials and end products are sensitive to hydrolysis and oxidation, it can be expedient to employ a protective gas atmosphere. However, such a procedure is in no way necessary for a successful outcome of the reaction. Nitrogen and argon are particularly suitable as protective gas. The reaction temperature is generally between 20° and 125° C., but preferably between 30° and 70° C.

For preparing the aryl esters of the phosphonous halides I, in the second step, the solution or suspension of Grignard compound is added, with intimate mixing, to the aryl ester of the phosphorous dihalide II, which is advantageously diluted with an inert, aprotic solvent, for example hexane, toluene, xylene or one of the abovementioned ethers. The reaction temperature in this step is generally between −40° and +30° C., but preferably between −30° and 0° C. The reaction generally proceeds exothermically; accordingly, it can be expedient to control the course of the reaction by cooling. The most favorable results are achieved when the reaction partners are used in the stoichiometric quantities. However, it is also possible to use a reaction partner in excess; but generally no particular advantages are associated with this.

The mixture is expediently stirred until the reaction is complete, and the solution is then separated off from precipitated magnesium halide. The solvents can be removed from the filtrate in a conventional manner, advantageously by distillation, in particular under reduced pressure.

The synthesis of esters of phosphonous halides by reaction of esters of phosphorous dihalides with Grignard reagents has not been hitherto known. Apparently, because of the known easy exchangeability of the halogen or ester groups bound to the phosphorus, there has been a prejudice against such organometallic nucleophiles to the effect that even in the reaction of esters of phosphorous dihalides with only one equivalent of Grignard reagent it would be expected that yield-reducing side and secondary reactions (formation of phosphinous esters and phosphanes) would proceed to a great extent and, associated with this, that the yield of the desired product would be low (Houben-Weyl, "Methoden der organischen Chemie", [Methods in Organic Chemistry], Volume 12/1, p. 210 (1963)). In view of this background, it is particularly surprising that using the procebs of the present invention, starting from easily accessible aryl esters of phosphonous dihalides, aryl esters of phosphorous halides substituted as required can be made accessible in a simple manner.

The compounds I according to the invention are suitable as precursors for specific derivatives of phosphorous acids, which are described in Patent Applications P 39 28 291.0 and P 39 16 502.7 which have an earlier priority, but which were not published prior to the present application.

The aryl esters of phosphorous dihalides II used as starting materials are either known or can be prepared in accordance with Application P 39 28 291.0, which was not published prior to the present application, or can be prepared in a simple manner analogously from $PHal_3$ and the relative phenol.

EXAMPLES

General instructions for preparing the aryl esters of phosphonous halides

Under a nitrogen atmosphere and with exclusion of moisture, the corresponding Grignard compound was prepared from 250 mmol of organobromine compound and 250 mmol (=6.1 g) of magnesium filings in 170 ml of tetrahydrofuran. The resulting solution or suspension of the organometallic compound was then added to the solution of 250 mmol of the relevant aryl ester of phosphorous dihalide in 160 ml of n-hexane/tetrahydrofuran (4:1) in the course of 30 to 40 minutes at approximately −30° C. with vigorous stirring. To complete the reaction, the mixture was stirred for a further 1 hour at −20° to −10° C. and for a further 4 hours at room temperature. After filtration from the magnesium salt, which was rinsed using 100 ml of n-hexane, the solvents were distilled off first under a water-pump vacuum and then in a high vacuum. The crude reaction products were obtained as viscous oils or resins, which were characterized by $^{31}$P-NMR spectroscopy. When aryl esters of phosphorous dichlorides were reacted with organomagnesium bromides, the products, in addition to the relevant aryl ester of phosphonous chloride, sometimes contained the analogous bromide as a secondary component, the formation of which is due to halogen exchange processes; for preparaing stabilizers for polymers, such mixtures can be used without further purification without problem.

The product content of compound I (total halide: X=chlorine+X=bromine) was generally between 80 and 98% of total phosphorus.

For the chemical characterization, in selected cases, the aryl esters of phosphonous halides were converted by secondary reactions with amines into aryl esters of phosphonous amides or with phenols into diaryl esters of phosphonous acid, which have already been described in the German Applications P 39 28 291.0 and P 39 16 502.7, which were not published prior to the present application.

2′,4′-Di-tert-butylphenyl ester of 2,4,6-trimethyl1-phenylphosphonous chloride/bromide Starting from 49.7 g of bromomesitylene and 77 g of 2,4-di-tert-butylphenyl ester of phosphorous dichloride, approximately 98 g of a yellow resin having a content of 78% of the chloride [$^{31}$p-NMR: $\delta CDCl_3$=180.7 ppm] and 20% of the bromide [$^{31}$P-NMR: $\delta CDCl_3$185.2 ppm] were obtained.

$C_{23}H_{32}ClOP$(390.93); $C_{23}H_{32}BrOP$ (435.37)

2. 2′,4′-Di-tert-butylphenyl ester of 2,4,5-trimethyl-1-phenylphosphonous chloride/bromide Starting from 49.7 g of 1-bromo-2,4,5-trimethylbenzene and 77 g of 2,4-di-tert-butylphenyl ester of phosphorous dichloride, approximately 97 g of a yellow resin having a content of 69% of the chloride $^{31}$P-NMR: $\delta CDCl_3$=170.5 ppm] and 21% of the bromide [$^{31}$P-NMR $CDCl_3$=175.1 ppm) were obtained.

$C_{23}H_{32}ClOP$(390.93); $C_{23}H_{32}BrOP$ (435.37)

3. 2′,4′-Di-tert-butylphenyl ester of 1-naphthylphosphonous chloride/bromide

Starting from 51.8 g of bromonaphthalene and 77 g of ditert-butylphenyl ester of phosphorous dichloride, approximately 100 g of a viscous resin having a content of 64% of the chloride [$^{31}$P-NMR: $\delta CDCl_3$=170.4 ppm] and 32% of the bromide [$^{31}$P-NMR: $\delta CDCl_3$=173.2 ppm] were obtained. $C_{24}H_{28}ClOP$ (398.90); $C_{24}H_{28}BrOP$ (443.35)

4. 2′,4′-Di-tert-butylphenyl eater of 2,5-dimethyl1-phenylphosphonous chloride/bromide Starting from 46.3 g of 1-bromo-2,5-dimethylbenzene and 77 g of 2,4-di-tert-butylphenyl ester of phosphorous dichloride, approximately 96 g of a yellow resin having a content of approximately 55% of the chloride [$^{31}$P-NMR: $\delta CDCl_3$=169 ppm], and 25% of the bromide [$^{31}$P-NMR: $\delta CDCl_3$173.0 ppm] were obtained.

$C_{22}H_{30}ClOP$ (376.90); $C_{22}H_{30}BrOP$ (421.35)

5. 2′,4′-Di-tert-butylphenyl ester of 2-methyl-1-phenylphosphonous chloride/bromide:

Starting from 42.8 g of 2-bromotoluene and 77 g of 2,4-di-tert-butylphenyl ester of phosphorous dichloride, approximately 92 g of a yellowish resin having a content of 63% of the chloride [$^{31}$P-NMR: $\delta CDCl_3$=168.3 ppm), and 22% of the bromide [$^{31}$P-NMR: δCDCl$_3$ 172.3 ppm] were obtained.

C$_{21}$H$_{28}$ClOP (362.88); C$_{21}$H$_{28}$BrOP (407.32)

6. 2',4'-Di-tert-butylphenyl ester of 2,4-dimethyl-1-phenylphosphonous chloride/bromide Starting from 46.3 g of 1-bromo-2,4-dimethylbenzene and 77 g of 2,4-di-tert-butylphenyl ester of phosphorous dichloride, approximately 96 g of a yellowish resin having a content of 63% of the chloride [$^{31}$P-NMR: δCDCl$_3$ 170.0 ppm), and 24% of the bromide [$^{31}$NMR: δCDCl$_3$ 174.7 ppm) were obtained.

C$_{22}$H$_{30}$ClOP (376.90); C$_{22}$H$_{30}$BrOP (421.35)

7. 2',4'-Di-tert-butylphenyl ester of 4-methyl-1-naphthylphosphonous chloride/bromide Starting from 55.3 g of 1-bromo-4-methylnaphthalene and 77 g of 2,4-di-tert-butylphenyl ester of phosphorous dichloride, approximately 100 g of yellowish resin having a content of 65% of the chloride [$^{31}$P-NMR: δCDCl$_3$ = 171.6 ppm), and 25% of the bromide [$^{31}$P-NMR: δCDCl$_3$ = 174.7 ppm].

C$_{25}$H$_{30}$ClOP (412.93); C$_{25}$H$_{30}$BrOP (457.38)

8. 2',4'-Di-tert-butylphenyl ester of 1-naphthylphosphonous bromide

Starting from 51.8 g of 1-bromonaphthalene and 99 g of 2,4-di-tert-butylphenyl ester of phosphorous dibromide, approximately 110 g of beige resin having a content of 88% of the above compound were obtained [$^{31}$P-NM: δCDCl$_3$: 173.2 ppm].

C$_{24}$H$_{28}$BrOP (443.37)

9. 2',4'-Di-tert-butylphenyl ester of 2,4,6-trimethyl-1-phenylphosphonous bromide Starting from 49.7 g of bromomesitylene and 99 g of 2,4-di-tert-butylphenyl ester of phosphorous dibromide, approximately 108 g of a yellow, viscous oil having a content of 92% of the above compound were obtained [$^{31}$P-NMR: δCDCl$_3$ = 185.2 ppm].

C$_{23}$H$_{32}$BrOP (435.37)

Exemplary secondary reactions of the aryl esters of phosphonous halides I according to the invention with secondary amines to give aryl esters of phosphonous amides, or with phenols to give diaryl esters of phosphonous acid General procedural instructions: The solution of 240 mmol of the relevant amine or phenol and 24.3 g (=240 mmol) of triethylamine in 100 ml of toluene were added dropwise in the course of 20 minutes to the solution of approximately 240 mmol of the relevant aryl ester of phosphonous halide or halide mixture in 250 ml of toluene stirred at −10° to −5° C. with exclusion of moisture under a nitrogen atmosphere. The mixture was then stirred for a further 4 hours at room temperature and then the solution was filtered off from precipitated ammonium salt, which was rinsed with a little toluene. The solvent was removed from the filtrate firstly under a water pump vacuum and then in a high vacuum. The remaining crude reaction products were first characterized by $^{31}$P-NMR spectroscopy and then purified by crystallization.

1. (2,4,6-Trimethyl-1-phenyl)morpholinophosphinous acid 2',4'-di-tert-butylphenyl ester Starting from 96 g of crude product according to Example 1 and 20.9 g of morpholine, approximately 105 g of a yellowish resin having a content of approximately 94% of the above compound were obtained. Crystallization from acetonitrile yielded colorless crystals of melting point 85°–87° C.

Analogously, from 104.5 g of crude product from Example 9, a yellowish resin having a content of 90% of the above compound were obtained.

2. (2,4,5-Trimethyl-1-phenyl)morpholinophosphinous acid 2',4'-di-tert-butylphenyl ester Starting from 96.5 g of crude product according to Example 2 and 20.9 g of morpholine, approximately 103 g of a yellowish resin having a content of approximately 84% of the above compound were obtained. Crystallization from acetonitrile yielded colorless crystals of melting point 132°–133° C.

3. Homopiperidino-(1-naphthyl)phosphinous acid 2,4-di-tert-butylphenyl ester Starting from 100 g of crude-product according to Example 3 and 23.8 g of hexmethyleneimine, approximately 107 g of beige resin having a content of 87% of the above compound were obtained. Crystallization from acetonitrile yielded colorless crystals of melting point 111°–113° C.

4. Bis(2',4'-di-tert-butylphenyl) (1-naphthyl)phosphonite

Starting from 106.5 g of crude product according to Example 8 and 49.5 g of 2,4-di-tert-butylphenol, approximately 135 g of beige resin having a content of 88% of the above compound were obtained. Crystallization from acetonitrile/acetone (5:1) yielded colorless crystals of melting point 125°–127° C.

We claim:

1. An aryl ester of a phosphonous halide of the formula I

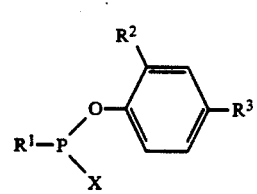

in which

R$^1$ is naphthyl or a naphthyl radical bearing 1 to 5 substituents, where the substituents are identical or different and are a non-aromatic hydrocarbon radical, an alkoxy radical or alkylthio radical each having 1 to 8 carbon atoms, aryl or aryloxy each having 6 to 10 carbon atoms or halogen having an atomic number from 9 to 35, R$^2$ is a non-aromatic hydrocarbon radical having 1 to 18 carbon atoms, aryl, arylmethyl, arylethyl or arylisopropyl, where each aryl contains 6 to 10 carbon atoms, R$^3$ is hydrogen or one of the groups mentioned under R$^2$ and X is chlorine or bromine.

2. A compound as claimed in claim 1, wherein R$^2$ is a tertiary alkyl radical having 4 to 10 carbon atoms.

* * * * *